United States Patent [19]

Rosen

[11] Patent Number: 5,688,804
[45] Date of Patent: Nov. 18, 1997

[54] 3-BENZYLAMINO-2-PHENYL-PIPERIDINE DERIVATIVES AS SUBSTANCE P RECEPTOR ANTAGONISTS

[75] Inventor: Terry J. Rosen, Burlingame, Calif.

[73] Assignee: Pfizer Inc., New York, N.Y.

[21] Appl. No.: 379,625

[22] PCT Filed: Jun. 3, 1993

[86] PCT No.: PCT/US93/05077

§ 371 Date: Jan. 31, 1995

§ 102(e) Date: Jan. 31, 1995

[87] PCT Pub. No.: WO94/03445

PCT Pub. Date: Feb. 17, 1994

Related U.S. Application Data

[63] Continuation of Ser. No. 924,773, Aug. 4, 1992, abandoned.

[51] Int. Cl.$^6$ ................ A61K 31/445; C07D 211/14
[52] U.S. Cl. ............... 514/272; 514/212; 514/326; 540/605; 544/330; 544/332; 546/209
[58] Field of Search ...................... 514/212, 272, 514/326; 540/605; 544/330, 332; 546/209

[56] References Cited

U.S. PATENT DOCUMENTS

| | | | |
|---|---|---|---|
| 3,560,510 | 2/1971 | Warawa et al. | 546/133 |
| 4,358,446 | 11/1982 | Haken et al. | 546/337 |
| 4,552,960 | 11/1985 | Krumkalns et al. | 544/336 |
| 4,680,283 | 7/1987 | Veber et al. | 514/17 |
| 5,138,060 | 8/1992 | Godek et al. | 514/305 |
| 5,232,929 | 8/1993 | Rosen et al. | 514/314 |
| 5,364,943 | 11/1994 | Rosen et al. | 546/223 |

FOREIGN PATENT DOCUMENTS

| | | |
|---|---|---|
| 0015628 | 9/1980 | European Pat. Off. |
| 0100158 | 2/1984 | European Pat. Off. |
| WO 092/01688 | 2/1992 | WIPO |
| WO 092/06079 | 4/1992 | WIPO |
| WO 092/12151 | 7/1992 | WIPO |
| WO 092/15585 | 9/1992 | WIPO |
| WO 092/17449 | 10/1992 | WIPO |
| WO 093/00330 | 1/1993 | WIPO |
| WO 093/00331 | 1/1993 | WIPO |

OTHER PUBLICATIONS

E. J. Warawa et al., "Quinuclidine Chemistry", J. Med. Chem., 18, 587 (1975).

Sandberg et al., "Substance P", J. Med. Chem., 25, 1009, (1982).

P. J. Goadsby et al., "Release of Vasoactive Peptides", Ann. Neurol., 23, 193 (1988).

Regoli, "Neurokinin Agonists & Antagonists", Elsevier Scientific Publishers, Amsterdam, pp. 85–95 (1987).

L. S. Trifonov et al., "Synthesis of 1,2-Five-Ring-Annellated Barrelenes", Helvetica Chimica Acta, 70, 4, 1732–1736 (1987).

A. S. Yanni et al., "Synthesis & Biological Activity", Indian J. Chem., 21B (7), 705–6, (1982).

Y. P. Gupta et al., "Synthesis of 2,12-Diazachrysene via Benzene Cyclization Reaction", Indian J. Chem., 19B (5), 400–1, (1980).

V. N. Gogte et al., "Infrared Spectral Study of the Effect of Substitution on Conformation and Hydrogen Bonding in 3-(aryl-amino)propanols", Indian J. Chem. 17B (3), 230–2, (1979).

S. V. Kessar et al., "New Routes to Condensed Polynuclear Compounds", Tetrahedron, 29, Pergamon Press, (GB), 419–424.

G. N. Walker et al., "Synthesis of Carried Heterocyclic & Substituted Arylalkyl", J. Med. Chem., 9, No. 4, (1966), 624–630.

G. N. Walker et al., "Application of Sodium Borohydride", Journal of Organic Chemistry, 26, No. 8, (1961), American Chemical Society, (US), 2740–2747.

Suman Rakhit et al., "Formation of Animals from Amines via Pummerer Rearrangement", Can. J. Chem., 57, No. 10, 1153 (1979).

*Primary Examiner*—Yogendra N. Gupta
*Attorney, Agent, or Firm*—Peter C. Richardson; Paul H. Ginsburg; B. Timothy Creagan

[57] ABSTRACT

The present invention relates to the derivatives of the compound of formula (I), which are useful in the treatment of inflammatory and central nervous system disorders, as well as other diorders

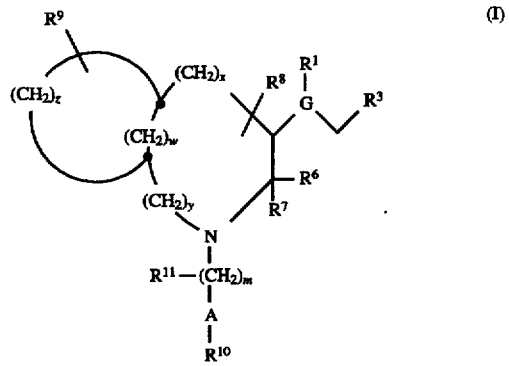

7 Claims, No Drawings

3-BENZYLAMINO-2-PHENYL-PIPERIDINE DERIVATIVES AS SUBSTANCE P RECEPTOR ANTAGONISTS

This application is a § 371 application of PCT/US93/05077, filed Aug. 4, 1992, and published as WO 94/03445 on Feb. 17, 1994 which is a continuation of U.S. patent application Ser. No. 07/924,773, filed Aug. 4, 1992, now abandoned.

BACKGROUND OF THE INVENTION

The present invention relates to novel substituted derivatives of nitrogen containing heterocycles, pharmaceutical compositions comprising such compounds and the use of such compounds in the treatment and prevention of inflammatory and central nervous system disorders, as well as several other disorders. The pharmaceutically active compounds of this invention are substance P receptor antagonists.

Substance P is a naturally occurring undecapeptide belonging to the tachykinin family of peptides, the latter being named because of their prompt stimulatory action on smooth muscle tissue. More specifically, substance P is a pharmacologically active neuropeptide that is produced in mammals (having originally been isolated from gut) and possesses a characteristic amino acid sequence that is illustrated by D. F. Veber et al. in U.S. Pat. No. 4,680,283. The wide involvement of substance P and other tachykinins in the pathophysiology of numerous diseases has been amply demonstrated in the art. For instance, substance P has recently been shown to be involved in the transmission of pain or migraine (see B. E. B. Sandberg et al., *Journal of Medicinal Chemistry*, 25, 1009 (1982)), as well as in central nervous system disorders such as anxiety and schizophrenia, in respiratory and inflammatory diseases such as asthma and rheumatoid arthritis, respectively, in rheumatic diseases such as fibrositis, and in gastrointestinal disorders and diseases of the GI tract such as ulcerative colitis and Crohn's disease, etc. (see D. Regoli in "Trends in Cluster Headache," edited by F. Sicuteri et al., Elsevier Scientific Publishers, Amsterdam, pp. 85–95 (1987)).

Quinuclidine derivatives and related compounds that exhibit activity as substance P receptor antagonists are referred to in PCT Patent Application PCT/US 89/05338, filed Nov. 20, 1989 and U.S. patent application Ser. No. 557,442, filed Jul. 23, 1990. Similar compounds are referred to in the PCT Application PCT/US91/02853, filed on Apr. 25, 1991 and PCT Application PCT/US91/03369, filed on May 14, 1991.

Monocyclic piperidine compounds are referred to in European Patent Publication 0,436,334 published on Jul. 10, 1990.

Piperidine derivatives and related heterocyclic nitrogen containing compounds that are useful as substance P antagonists are referred to in U.S. patent application Ser. No. 619,361, filed Nov. 28, 1990, U.S. patent application Ser. No. 590,423, filed Sep. 28, 1990, U.S. patent application Ser. No. 717,943 filed Jun. 20, 1991, U.S. patent application Ser. No. 719,884 filed on Jun. 21, 1991, and U.S. patent application Ser. No. 724,268 filed Jul. 1, 1991.

Compounds containing a sulfur or an oxygen group at the 3 position of a nitrogen containing ring are referred to in European Patent Publications 520,555A1 published on Dec. 12, 1992, 499,313A1 published on Aug. 19, 1992, and 528,495A1 published on Feb. 24, 1993.

SUMMARY OF THE INVENTION

The present invention relates to compounds of the formula

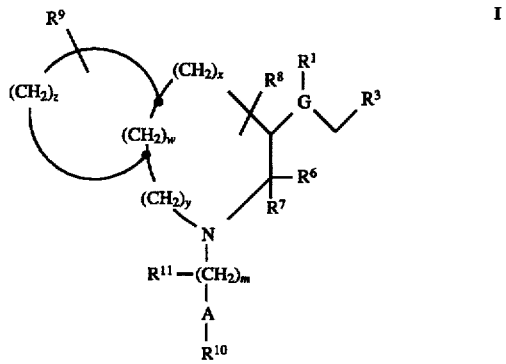

I wherein m is an integer from 1 to 8, any one of the carbon—carbon single bonds of $(CH_2)_m$ may optionally be replaced by a carbon—carbon double bond or a carbon—carbon triple bond, and any one of the carbon atoms of said $(CH_2)_m$ may optionally be substituted with $R^{11}$;

w is an integer from zero to four;

x is an integer from zero to four;

y is an integer from zero to four;

z is an integer from zero to six and wherein the ring containing $(CH_2)_z$ may contain from zero to three double bonds, and one of the carbons of $(CH_2)_z$ may optionally be replaced by oxygen, sulfur or nitrogen;

$R^1$ is hydrogen or $(C_1–C_8)$ alkyl optionally substituted with hydroxy, alkoxy or fluoro;

$R^3$ is aryl selected from phenyl, indanyl, and naphthyl; heteroaryl selected from benzothienyl, benzofuryl, thienyl, furyl, pyridyl, thiazolyl, isothiazolyl, oxazolyl, isoxazolyl, triazolyl, tetrazolyl, and quinolyl; or cycloalkyl having from three to seven carbon atoms, wherein one of said carbon atoms may optionally be replaced by nitrogen, oxygen or sulfur; wherein each of said aryl and heteroaryl groups may optionally be substituted with one or more substituents, and said $(C_3–C_7)$cycloalkyl may optionally be substituted with one or two substituents, said substituents being independently selected from halo, nitro, $(C_1–C_{10})$alkyl optionally substituted with from one to three fluorine atoms, $(C_1–C_{10})$alkoxy optionally substituted with from one to three fluorine atoms, trifluoromethyl, amino, $(C_1–C_6)$-alkylamino, di$(C_1–C_6)$alkylamino,

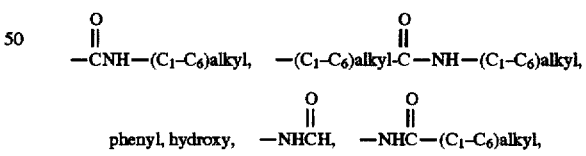

hydroxy $(C_1–C_6)$alkyl, and $(C_1–C_6)$alkoxy$(C_1–C_6)$alkyl;

$R^6$ is a functionality selected from hydrogen, $(C_1–C_6)$ straight or branched alkyl, $(C_3–C_7)$cycloalkyl wherein one of the carbon atoms may optionally be replaced by nitrogen, oxygen or sulfur; aryl selected from biphenyl, phenyl, indanyl and naphthyl; heteroaryl selected from benzothienyl, thienyl, furyl, benzofuryl, pyridyl, thiazolyl, isothiazolyl, oxazolyl, isoxazolyl, triazolyl, tetrazolyl and quinolyl; phenyl $(C_2–C_6)$ alkyl, benzhydryl and benzyl, wherein each of said aryl and heteroaryl groups and the phenyl moieties of said benzyl, phenyl$(C_2–C_6)$alkyl and benzhydryl may optionally be substituted with one or more substituents independently selected from halo, nitro, $(C_1-C_{10})$alkyl optionally substituted with from one to three fluorine atoms, $(C_1-C_{10})$alkoxy optionally substituted with from one to three fluorine atoms, amino, hydroxy $(C_1-C_6)$ alkyl, $(C_1-C_6)$alkoxy$(C_1-C_6)$alkyl, $(C_1-C_6)$-alkylamino,

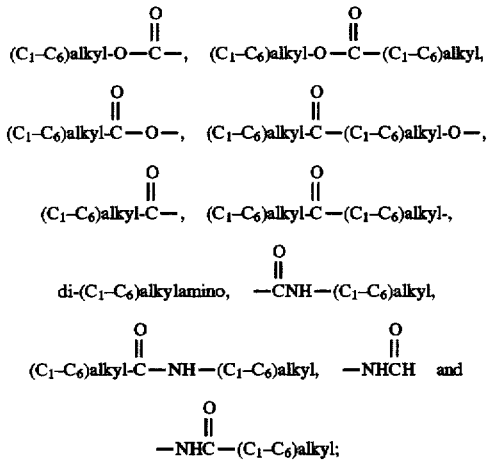

and wherein one of the phenyl moieties of said benzhydryl may optionally be replaced by naphthyl, thienyl, furyl or pyridyl;

$R^7$ is hydrogen, phenyl or $(C_1-C_6)$alkyl;

or $R^6$ and $R^7$, together with the carbon to which they are attached, form a saturated carbocyclic ring having from 3 to 7 carbon atoms wherein one of said carbon atoms may optionally be replaced by oxygen, nitrogen or sulfur;

$R^8$ may be attached to any atom of the nitrogen containing ring having an available bonding site and $R^9$ may be attached to any atom of the $(CH_2)_z$ containing ring having an available bonding site or to any carbon atom of the nitrogen containing ring having an available bonding site;

$R^8$ and $R^9$ are independently selected from hydrogen, hydroxy, halo, amino, oxo (=O), cyano, hydroxy-$(C_1-C_6)$ alkyl, $(C_1-C_6)$alkoxy-$(C_1-C_6)$alkyl, $(C_1-C_6)$alkylamino, di-$(C_1-C_6)$alkylamino, $(C_1-C_6)$alkoxy,

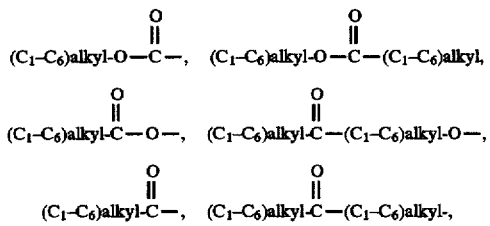

and the functionalities set forth in the definition of $R^6$;

A is selected from the group consisting of $CH_2$, nitrogen, oxygen, sulfur and carbonyl;

G is nitrogen, oxygen or sulfur;

$R^{10}$ is a monocyclic or bicyclic heterocycle selected from the group consisting of pyrimidinyl, benzoxazolyl, 2,3-dihydro-3-oxobenzisosulfonazol-2-yl, morpholin-1-yl, thiomorpholin-1-yl, benzofuranyl, benzothienyl, indolyl, isoindolyl, isoquinolinyr, furyl, pyridyl, isothiazolyl, oxazolyl, triazolyl, tetrazolyl, quinolyl, thiazolyl, thienyl, and groups of the formulae

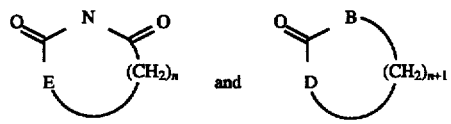

wherein B and D are selected from carbon, oxygen and nitrogen, and at least one of B and D is other than carbon; E is carbon or nitrogen; n is an integer from 1 to 5; any one of the carbon atoms of said $(CH_2)_n$ and $(CH_2)_{n+1}$ may be optionally substituted with $(C_1-C_6)$alkyl or $(C_2-C_6)$ spiroalkyl; and either any one pair of the carbon atoms of said $(CH_2)_n$ and $(C_2)_{n+1}$ may be bridged by a one or two carbon atom linkage, or any one pair of adjacent carbon atoms of said $(CH_2)_n$ and $(C_2)_{n+1}$ may form, together with from one to three carbon atoms that are not members of the carbonyl containing ring, a $(C_3-C_5)$ fused carbocyclic ring;

$R^{11}$ is oximino (=NOH) or one of the functionalities set forth in any of the definitions of $R^6$, $R^8$ and $R^9$;

with the proviso that (a) neither $R^8$, $R^9$, $R^{10}$ nor $R^{11}$ can form, together with the carbon to which it is attached, a ring with $R^7$, (b) when z is other than zero, $R^9$ must be attached to the $(CH_2)_z$ containing ring and $R^8$ and $R^9$ cannot be attached to the same carbon atom, (c) when both z is zero and $R^8$ and $R^9$ are attached to the same carbon atom, then either each of $R^8$ and $R^9$ is independently selected from hydrogen, fluoro, $(C_1-C_6)$alkyl, hydroxy-$(C_1-C_6)$alkyl and $(C_1-C_6)$alkoxy-$(C_1-C_6)$alkyl, or $R^8$ and $R^9$, together with the carbon to which they are attached, form a $(C_3-C_6)$ saturated carbocyclic ring that forms a spiro compound with the nitrogen containing ring to which they are attached, (d) when A is nitrogen, sulfur, or oxygen, m is greater than one, (e) when A is $CH_2$ or carbonyl then $R^{10}$ must be substituted or unsubstituted pyrimidinyl, benzoxazolyl, 2,3-dihydro-3-oxobenzisosulfonazol-2-yl, morpholin-1-yl, thiomorpholin-1-yl, benzofuranyl, benzothienyl, indolyl, isoindolyl, isoquinolinyl or

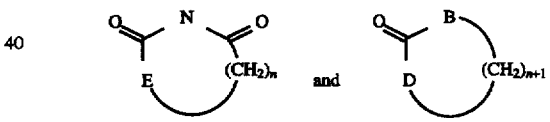

wherein B and D are selected from carbon, oxygen, and nitrogen, and at least one of B and D is other than carbon; E is carbon or nitrogen; n is an integer from 1 to 5; and any one of the carbons of the $(CH_2)_n$ or $(CH_2)_{n+1}$ may be optionally substituted with $(C_1-C_6)$alkyl or $(C_2-C_6)$ spiroalkyl, and either any two of the carbon atoms of said $(C_2)_n$ and $(CH_2)_{n+1}$ may be bridged by a one or two carbon atom linkage, or any one pair of adjacent carbons of said $(C_2)_n$ and $(CH_2)_{n+1}$ may form, together with from one to three carbon atoms that are not members of the carbonyl containing ring, a $(C_3-C_5)$ fused carbocyclic ring, (f) when w is other than zero, then y is zero, the sum of w and z is less than 7, x is an integer from 0 to 2, z is an integer from 1 to 4, and wherein the ring containing $(CH_2)_z$ is a saturated ring wherein no carbon atom may be replaced by oxygen, sulfur or nitrogen, and wherein $R^8$ is optionally only a substituent on one of the carbon atoms of said $(CH_2)_z$, and (g) when G is oxygen or sulfur then $R^1$ is absent.

Preferred compounds of the formula I are those wherein z is zero, G is nitrogen, and $R^9$ is attached to the ring to which $R^6$ and $R^7$ are attached.

Preferred compounds of the formula I are those wherein m is an integer from 4 to 6; G is nitrogen; $R^3$ is phenyl optionally substituted with one or two substituents, said substituents being independently selected from halo, nitro, $(C_1-C_{10})$ alkyl optionally substituted with from one to three fluorine atoms, $(C_1-C_{10})$ alkoxy optionally substituted with from one to three fluorine atoms, trifluoromethyl, amino, $(C_1-C_6)$-alkylamino, di$(C_1-C_6)$alkylamino,

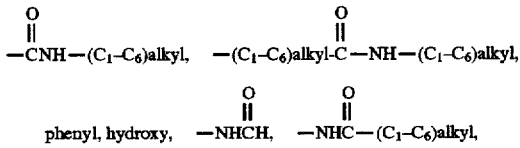

hydroxy$(C_1-C_6)$alkyl and $(C_1-C_6)$alkoxy$(C_1-C_6)$alkyl; $R^6$ is phenyl, $R^7$ is hydrogen, and $R^1$ is hydrogen.

More preferred compounds of formula I are the foregoing compounds wherein x is zero to two, w, y end z are zero and $R^8$, $R^9$ and $R^{11}$ are hydrogen.

Specific preferred compounds of the formula I are:

(2S, 3S)-3-(2-methoxybenzyl)amino-2-phenyl-1-[4-(thiazol-2-yl)aminobutyl]piperidine;

(2S,3S)-3-(2-methoxybenzyl)amino-2-phenyl-1-[4-(pyrimidin-2-yl)aminobutyl]piperidine;

cis-1-[4-(benzoxazol-2-yl) aminobutyl]-3-(2-methoxybenzyl)amino-2-phenylpiperidine;

(2S,3S)-1-[2,3-(dihydro-3-oxobenzisosulfonazol-2-yl)butyl]-3-(2-methoxybenzyl)amino-2-phenylpiperidine;

cis-3-(2-methoxybenzyl)amino-2-phenyl-1-[4-(succinimido-1-yl-butyl]piperidine;

(2S,3S)- 1-(5,6-carbonyldioxyhexyl)-3-(2-methoxybenzyl)amino-2-phenylpiperidine;

Other compounds of formula I are:

[1α, 3α, 4α, 5α]-4-(5-tert-butyl-2-methoxybenzyl) amino-3-phenyl-2-[4-(thiazol-2-yl)aminobutyl]-2-azabicyclo-[3.3.0]octane;

4-(2-methoxy-5-trifluoromethoxybenzyl)amino-3-phenyl-2-[4-(pyrimidin-2-yl)aminobutyl]-2-azabicyclo[4.4.0]decane;

4-benzhydryl-3-[4-(thiazol-2-yl)aminobutyl]-5-(2-trifluoromethoxybenzyl)amino-3-azabicyclo[4.1.0]heptane;

1-(5,6-carbonyldioxyhexyl)-3-(2-cyclopropylmethoxy-5-trifluoromethoxybenzyl)amino-2-phenylpiperidine;

3-(2,4-dimethoxybenzyl)amino-2-phenyl-1-[4-(pyrimidin-2-yl)aminopentyl]pyrrolidine;

1-[4-(glutarimido-1-yl)butyl]-3-(2-methoxybenzyl) amino-2-phenylpiperidine;

2-benzhydryl-3-(5-cyclopropylmethoxy-2-isopropoxy)-2-[4-(thiazol-2-yl)aminobutyl]-2-azabicyclo[3.3.0]octane.

Compounds of formula I are basic in nature. The present invention, therefore, also relates to the pharmaceutically acceptable acid addition salts of compounds of the formula I. The acids which are used to prepare the pharmaceutically acceptable acid addition salts of the basic compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The term "halo", as used herein, unless otherwise indicated, includes chloro, fluoro, bromo and iodo.

The term "alkyl", as used herein, unless otherwise indicated, includes saturated monovalent hydrocarbon radicals having straight, branched or cyclic moieties or combinations thereof.

The term "one or more substituents," as used herein, includes from one to the maximum number of substituents possible based on the number of available bonding sites.

The present invention also relates to a pharmaceutical composition for treating or preventing a condition selected from the group consisting of urinary incontinence, inflammatory diseases (e.g., arthritis, psoriasis, asthma and inflammatory bowel disease), reflux gastroesophogal disease, hypertension, anxiety, depression or dysthymic disorders, cluster headache, colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising an amount of a compound of the formula I, or a pharmaceutically acceptable salt thereof, effective in treating or preventing such condition, and a pharmaceutically acceptable carrier.

The present invention also relates to a method of treating or preventing a condition selected from the group consisting of urinary incontinence, inflammatory diseases (e.g., arthritis, psoriasis, asthma and inflammatory bowel disease), reflux gastroesophogal disease, hypertension, anxiety, depression or dysthymic disorders, cluster headache, colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising administering to said mammal an amount of a compound of the formula I, or a pharmaceutically acceptable salt thereof, effective in treating or preventing such condition.

The present invention also relates to a pharmaceutical composition for antagonizing the effects of substance P in a mammal, including a human, comprising a substance P antagonizing amount of a compound of the formula I, or a pharmaceutically acceptable salt thereof, and a pharmaceutically acceptable carrier.

The present invention also relates to a method of antagonizing the effects of substance P in a mammal, including a human, comprising administering to said mammal a substance P antagonizing amount of a compound of the formula I, or a pharmaceutically acceptable salt thereof.

The present invention also relates to a pharmaceutical composition for treating or preventing a condition selected from the group consisting of urinary incontinence, inflammatory diseases (e.g., arthritis, psoriasis, asthma and inflammatory bowel disease), anxiety, depression or dysthymic disorders, cluster headache, colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising an amount of a compound of the formula I, or a pharmaceutically acceptable salt thereof, effective in antagonizing the effect of substance P at its receptor site, and a pharmaceutically acceptable carrier.

The present invention also relates to a method of treating or preventing a condition selected from the group consisting of urinary incontinence, inflammatory diseases (e.g., arthritis, psoriasis, asthma and inflammatory bowel disease), anxiety, depression or dysthymic disorders, cluster headache, colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising administering to said mammal an amount of a compound of the formula I, or a pharmaceutically acceptable salt thereof, effective in antagonizing the effect of substance P at its receptor site.

The present invention also relates to a pharmaceutical composition for treating or preventing a disorder in a mammal, including a human, the treatment or prevention of which is effected or facilitated by a decrease in substance P mediated neurotransmission, comprising an amount of a compound of the formula I, or a pharmaceutically acceptable salt thereof, effective in antagonizing the effect of substance P at its receptor site, and a pharmaceutically acceptable carrier.

The present invention also relates to a method of treating or preventing a disorder in mammal, including a human, the treatment or prevention of which is effected or facilitated by a decrease in substance P mediated neurotransmission, comprising administering to said mammal an amount of a compound of the formula I, or a pharmaceutically acceptable salt thereof, effective in antagonizing the effect of substance P at its receptor site.

The present invention also relates to a pharmaceutical composition for treating or preventing a disorder in a mammal, including a human, the treatment or prevention of which is effected or facilitated by a decrease in substance P mediated neurotransmission, comprising an amount of a compound of the formula I, or a pharmaceutically acceptable salt thereof, effective in treating or preventing such disorder, and a pharmaceutically acceptable carrier.

The present invention also relates to a method of treating or preventing a disorder in mammal, including a human, the treatment or prevention of which is effected or facilitated by a decrease in substance P mediated neurotransmission, comprising administering to said mammal an amount of a compound of the formula I, or a pharmaceutically acceptable salt thereof, effective in treating or preventing such disorder.

The compounds of the formula I have chiral centers and therefore exist in different enantiomeric forms. This invention relates to all optical isomers and all stereoisomers of compounds of the formula I, and mixtures thereof.

DETAILED DESCRIPTION OF THE INVENTION

The compounds of the formula I may be prepared as described in the following reaction schemes and discussion. Unless otherwise indicated, $R^1$, $R^3$, $R^6$, $R^7$, $R^8$, $R^9$, $R^{10}$, $R^{11}$, m, w, x, y, and z in the reaction schemes and discussion that follow are defined as above.

SCHEME 1

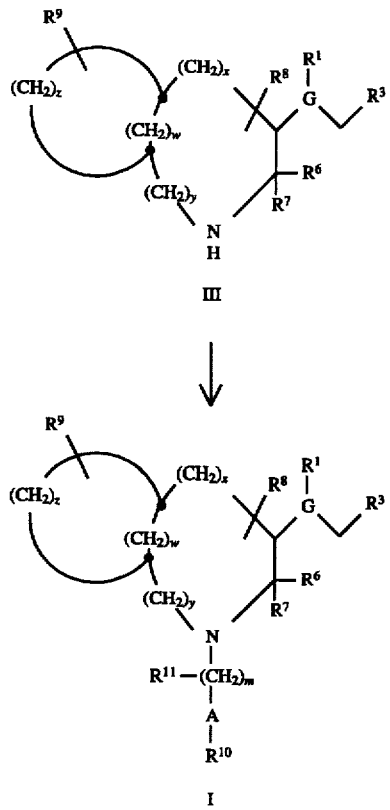

SCHEME 2
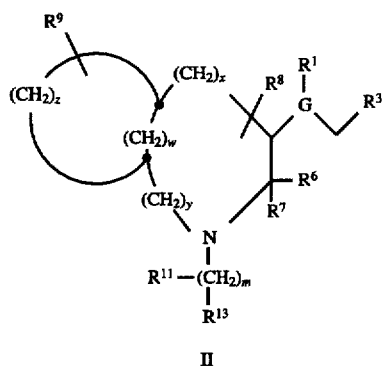
II
↓
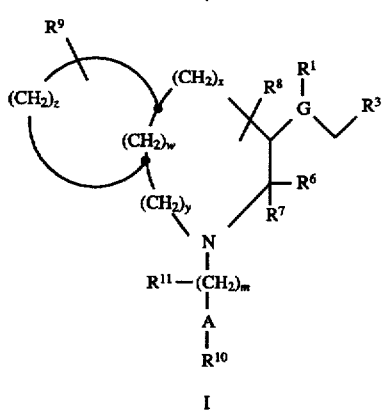
I
SCHEME 3
III
↓
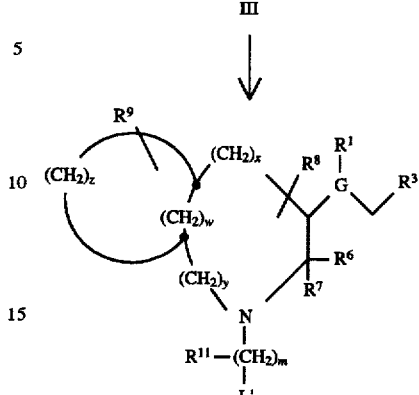
IV
↓
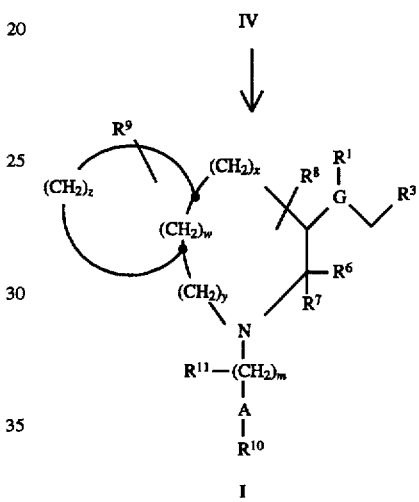
I
SCHEME 4
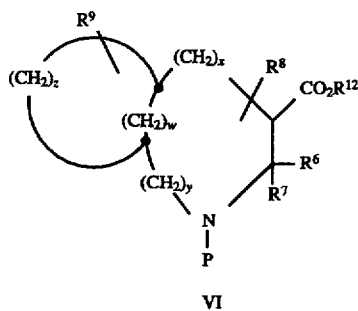
VI

-continued
SCHEME 4

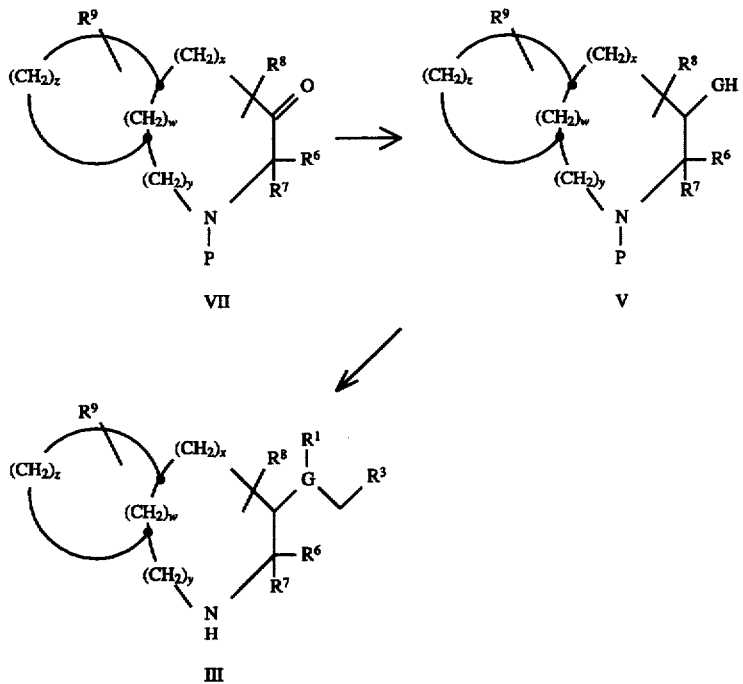

The starting materials of the formula III wherein B is nitrogen and w and z equal zero may be prepared as described in U.S. patent application Ser. No. 619,361, filed Nov. 28, 1990, U.S. patent application Ser. No. 675,244, filed Mar. 26, 1991, U.S. patent application Ser. No. 717,943 filed on Jun. 20, 1991 and, U.S. patent application Ser. No. 719,884 filed on Jun. 21, 1991. These applications are incorporated herein in their entirety.

The starting materials of the formula III wherein B is nitrogen, w is zero and z is other than zero may be prepared as described in U.S. patent application Ser. No. 590,423, filed Sep. 28, 1990 and, U.S. patent application Ser. No. 717,943 filed on Jun. 20, 1991. These applications are incorporated herein in their entirety.

The starting materials of the formula III wherein B is nitrogen, y is zero and w is other than zero can be prepared as described in United States Patent Application of M. Desai entitled Bridged Aza-Bicyclic Derivatives filed on May 18, 1992, which is incorporated herein by reference in its entirety.

Referring to Scheme 1, the compounds of formula III may be converted to compounds of the formula I having the same stereochemistry by reacting them with the appropriate compound of the

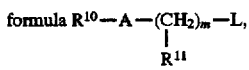

wherein L is halo, mesylate or tosylate and wherein any one of the carbon—carbon single bonds of said $(CH_2)_m$ may optionally be replaced by a carbon—carbon double bond, and wherein any one of the carbons of said $(CH_2)_m$ may optionally be substituted with $R^{11}$. This reaction is typically carried out in the presence of a base such as triethylamine, lithium diisopropylamine, sodium methoxide, potassium hydroxide or potassium t-butoxide, in a polar solvent such as t-butanol, dimethyl formamide (DMF), methylene chloride or dichloroethane, at a temperature from about room temperature to about 150° C. Preferably, the reaction is carried out at the reflux temperature in methylene chloride in the presence of triethylamine.

Scheme 2 illustrates an alternative method of converting compounds of formula III into compounds of the formula I having the same stereochemistry, and in which $R^{10}$ is a heteroaromatic group and A is selected from oxygen, nitrogen and sulfur, by first converting compounds of formula III into intermediates of formula II. These intermediates of formula II can then be converted into compounds of formula I.

Compounds of formula III are converted into compounds of formula II by reacting them with the appropriate compound of the

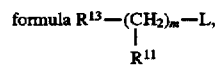

wherein L is halo, mesylate or tosylate and wherein one of the carbon—carbon single bonds of said $(CH_2)_m$ may optionally be replaced by a carbon—carbon double bond, and wherein one of the carbons of said $(CH_2)_m$ may optionally be substituted with $R^{11}$, and wherein $R^{13}$ is amino, hydroxyl or thiol, and wherein said hydroxyl, amino and thiol groups may be optionally protected as appropriate (e.g., t-butoxy carbonyl (BOC), trifluoroacetyl, carbobenzyloxy or carboethoxy). Preferred protecting groups for the hydroxyl, amino and thiol groups are t-butyldimethylsilyl, t-butoxycarbonyl and acetyl, respectively. This reaction is typically carried out in the presence of a base such as triethylamine or potassium t-butoxide, in a polar solvent such as methylene chloride, dichloroethane, tetrahydrofuran or chloroform, at a temperature from about room temperature to about 150° C. Preferably, the reaction is carried out at the reflux temperature in methylene chloride in the presence of triethylamine. The reaction is generally carried out for about 0.5 to about 72 hours.

When a protecting group is present, it is then removed from the compound of formula II. For the case of a t-butoxycarbonyl protected amino group, deprotection is accomplished by reacting the protected compound of formula II with an acid such as hydrochloric acid, trifluoroacetic acid or perchloric acid, to yield a compound of the formula II having the same stereochemistry in which the protecting group has been replaced with hydrogen. Appropriate solvents for this reaction include polar solvents such as methylene chloride, dioxane, ether or THF, preferably dioxane. A t-butyldimethylsilyl ether is cleaved by similar conditions or by using tetrabutylammonium fluoride, in tetrahydrofuran (THF). An acetyl-protected thiol is cleaved using methanolic sodium methoxide or aqueous ammonia. The deprotection reaction is typically run at a temperature from about −10° C. to about 50° C., preferably about 25° C., for about 0.5 to about 24 hours.

Intermediate compounds of formula II so formed can be converted into compounds of formula I by reacting them with the appropriate monocyclic or bicyclic heterocycle of the formula $R^{10}$-X wherein X is halo, mesylate, or tosylate and $R^{10}$ is defined as above. This reaction is typically carried out in the presence of a base such as triethylamine, lithium diisopropylamine, sodium methoxide, potassium hydroxide or potassium t-butoxide, in a polar solvent such as methylene chloride, t-butanol, dimethyl formamide (DMF) or dichloroethane, at a temperature from about room temperature to about 150° C. Preferably, the reaction is carried out at the reflux temperature in methylene chloride in the presence of triethylamine.

Alternatively, compounds of formula II in which $R^{13}$ is amino may be converted into compounds of formula I in which $R^{10}$ is a cyclic imido group such as succinimido by treating the compound of formula II with an appropriate dicarboxylic acid, an activated derivative of a dicarboxylic acid (e.g., dihalo, mesylate or tosylate), or an anhydride. This reaction is typically carried out in a non-polar solvent such as xylene, hexanes, cyclohexane, ether, tetrahydrofuran or toluene at a temperature from 60° C. to about the reflux temperature of the solvent.

Scheme 3 illustrates an alternative method of converting compounds of formula III into compounds of formula I, in which A is oxygen or nitrogen, by first treating compounds of formula III with a compound of

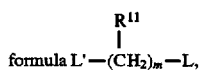

formula L'—(CH$_2$)$_m$—L, wherein L' is halo, mesylate or tosylate and L is defined as above, to give a compound of formula IV. This reaction is typically carried out in the presence of a base such as triethylamine, lithium diisopropylamine, sodium methoxide, potassium hydroxide or potassium t-butoxide, in a polar solvent such as t-butanol, dimethyl formamide (DMF), methylene chloride or dichloroethane, at a temperature from about room temperature to about 150° C. Preferably, the reaction is carried out at the reflux temperature in methylene chloride in the presence of triethylamine.

Compounds of formula IV may similarly be obtained by treating compounds of formula III with a compound of

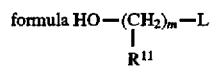

formula HO—(CH$_2$)$_m$—L in which the hydroxyl group may be protected as appropriate, preferably with the t-butyl dimethylsilyl group. This reaction is typically carried out in the presence of a base such as triethylamine, lithium diisopropylamine, sodium methoxide, potassium hydroxide or potassium t-butoxide, in a polar solvent such as t-butanol, dimethyl formamide (DMF), methylene chloride or dichloroethane, at a temperature from about room temperature to about 150° C. Preferably, the reaction is carried out at the reflux temperature in methylene chloride in the presence of triethylamine. After this initial reaction, the hydroxyl group can then be deprotected, if necessary, by any of the conventional means. Preferably, when the protecting group is t-butyldimethylsilyl, deprotection is carried out with tetrabutylammonium fluoride in tetrahydrofuran or with an acid such as hydrochloric acid (HCl) or acetic acid in a polar solvent such as water or tetrahydrofuran, at a temperature from about 0° C. to about 60° C., preferably at about room temperature. The free hydroxyl can then be converted into a leaving group by any of the conventional means. Treatment of the hydroxyl group with an agent such as methanesulfonyl chloride is preferred.

Compounds of formula IV are converted into compounds of formula I by reacting them with the appropriate compound of the formula $R^{10}$-A-H. This reaction is typically carried out in the presence of a base such as triethylamine or potassium t-butoxide, in a polar solvent such as methylene chloride, dichloroethane, tetrahydrofuran or chloroform, at a temperature from about room temperature to about 150° C. Preferably, the reaction is carried out at the reflux temperature in methylene chloride in the presence of triethylamine. The reaction is generally carried out for about 0.5 to about 72 hours.

Alternatively, compounds of formula IV are converted into compounds of formula I by reacting them with the corresponding anion derived from treatment of $R^{10}$-A-H with a base. Preferably, the anion can be formed with a reagent such as sodium hydride or butyl lithium in a solvent such as tetrahydrofuran or ether. This reaction is typically carried out in the presence of a base such as triethylamine, lithium diisopropylamine, sodium methoxide, potassium hydroxide or potassium t-butoxide, in a polar solvent such as methylene chloride, t-butanol, dimethyl formamide (DMF) or dichloroethane, at a temperature from about room temperature to about 150° C. Preferably, the reaction is carried out at the reflux temperature in methylene chloride in the presence of triethylamine.

Compounds of formula III may also be converted into the corresponding compounds of the formula I by first reacting them with the appropriate compound of the

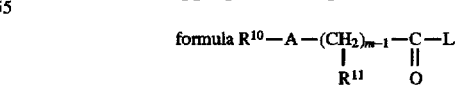

formula $R^{10}$—A—(CH$_2$)$_{m-1}$—C—L
                              |       ||
                              $R^{11}$  O wherein L is defined as above or is imidazole, and then reducing the resulting amide. This reaction is typically carried out in an inert solvent such as THF or dichloromethane at a temperature from about −20° C. to about 60° C. It is preferably carried out in dichloromethane at about 0° C. Reduction of the resulting amide is accomplished by treatment with a reducing agent such as borane dimethylsulfide complex, lithium aluminum hydride or diisobutylaluminum hydride in an inert solvent such as ethyl ether or THF. The reaction temperature may range from about 0° C. to about 60° C. Preferably, the reduction is accomplished using borane dimethylsulfide complex in THF at about 60° C.

Scheme 4 illustrates a method of preparing compounds of formula III wherein G is sulfur or oxygen, and $R^1$ is absent.

Compounds of formula III can be prepared from esters of formula VI wherein $R^{12}$ is ($C_1$–$C_4$)alkyl or phenyl and the ring nitrogen adjacent to $R^6$ and $R^7$ is protected with an appropriate protecting group P.

Esters of formula VI are hydrolyzed to form acids of formula VI, wherein $R^{12}$ is hydrogen, by methods well known to those skilled in the art, for example, by treatment of the ester of formula VI with an acid or a base in a solvent such as water.

The acids of formula VI, wherein $R^{12}$ is hydrogen, are oxidized to form a compound of formula V wherein G is oxygen by reacting the compound of formula VI with lead tetraacetate in an inert solvent such as cyclohexane, hexane, methylene chloride, or benzene at a temperature of 0° C. to a temperature of 90° C. Preferably, the oxidation of the compounds of formula is facilitated by the addition of copper (II) salts such as copper (II) acetate ($Cu(OCOCH_3)_2$) and pyridine.

The compound of formula V wherein G is oxygen is converted to a compound of formula III wherein $R^1$ is absent by alkylating the compound of formula V with a compound of formula $R^3CH_2X$ and a base, wherein X is a leaving group selected from halo and —$SO_3R^{12}$, wherein $R^{12}$ is ($C_1$–$C_4$) alkyl or phenyl, and $R^3$ is defined as above. The reaction of the compound of formula III with the compound of formula $R^3CH_2X$ is typically carried out in a solvent such as dichloromethane, chloroform, carbon tetrachloride, ether, hexane, cyclohexane or tetrahydrofuran, preferably tetrahydrofuran, at a temperature from about 0° C. to about 60° C., preferably at about 25° C. Suitable bases include sodium hydride, organolithium bases such as butyl lithium, alkali metal alkoxides such as potassium or sodium t-butoxide and organic bases such as triethylamine, diisopropylethylamine and hexamethyldisilazide. Non-nucleophilic bases such as triethylamine, diisopropylethylamine and hexamethyldisilazide are preferred because they will not react with the compound of formula II and this will not form the unwanted byproducts that result from such reaction.

Preferably, the conversion of the compound of formula V to the compound of formula III is facilitated by preforming the anion of formula V by the addition of a strong base such as sodium hydride.

The compound of formula III so formed is then deprotected by the procedure described above to form the free amine of formula III.

The amine of formula III can be converted to compounds of formula I by the procedures described in schemes 1 through 3 above.

Alternatively, compounds of formula V can be prepared by reducing a ketone of formula VII. Ketones of formula VII can be reduced with lithium aluminium hydride, borane dimethylsulfide in tetrahydrofuran (THF), borane in THF and sodium borohydride titanium tetrachloride. Best results are obtained using sodium borohydride in THF. The reaction may be carried out at temperatures from about −78° C. to about 80° C., and are preferably carried out at about 0° C. temperature of the solvent. Compounds of formula V so formed may be converted to compounds of formula III as described above.

Compounds of formula III wherein G is sulfur and $R^1$ is absent can be formed from compounds of formula V wherein G is sulfur. Compounds of formula V wherein G is sulfur may be prepared from compounds of formula VII wherein G is oxygen by reaction with phosphorus pentasulfide ($P_4S_{10}$) in pyridine, followed by reduction with sodium borohydride ($NaBH_4$). The temperature during the reaction with $P_4S_{10}$ is preferably about 90° C., but can range between about 0° C. to about 110° C.

Alternatively, compounds of formula V wherein G is sulfur can be prepared from compounds of formula VII wherein the ketone of formula VII is reacted with Lawesson's reagent in the presence of a base followed by reduction with sodium borohydride. The compounds of formula V wherein G is sulfur can be converted to compounds of formula III wherein G is sulfur by reaction of the compound of formula V with a compound of the formula $R^3CH_2X$ wherein X is a leaving group selected from halo and —$SO_3R^{12}$, $R^3$ is defined as above and $R^{12}$ is ($C_1$–$C_6$)alkyl or phenyl. The reaction of the compound of formula V with a compound of formula $R^3CH_2X$ is typically carried out in a solvent such as dichloromethane, chloroform, carbon tetrachloride, hexane, cyclohexane or tetrahydrofuran, preferably dichloromethane at a temperature from about 0° C. to about 60° C., preferably at about 25° C. The compound of formula III so formed is deprotected by the methods described above.

Alternatively, compounds of formula V wherein G is oxygen may be converted to compounds of formula III by reaction of the compound of formula V with mesylchloride followed by reaction with a thiol of formula $R^3CH_2SH$, wherein $R^3$ is defined as above. The reaction of the compound of formula V with the compound of formula $R^3CH_2SH$ is typically carried out in solvents such as dichloromethane, chloroform, carbon tetrachloride, hexane, cyclohexane or tetrahydrofuran, preferably dichloromethane at a temperature from about 0° C. to about 60° C., preferably at about 25° C. The compounds of formula III so formed can be deprotected to form compounds of formula III by the methods described above.

The compounds of formula III so formed may be converted to the final products of formula I by schemes 1 through 3, described above.

The preparation of other compounds of the formula I not specifically described in the foregoing experimental section can be accomplished using combinations of the reactions described above that will be apparent to those skilled in the art.

In each of the reactions discussed or illustrated in Schemes 1 to 4 above, pressure is not critical unless otherwise indicated. Pressures from about 0.5 atmospheres to about 5 atmospheres are generally acceptable, and ambient pressure, i.e. about 1 atmosphere, is preferred as a matter of convenience.

The novel compounds of the formula I and the pharmaceutically acceptable salts thereof are useful as substance P antagonists, i.e., they possess the ability to antagonize the effects of substance P at its receptor site in mammals, and therefore they are able to function as therapeutic agents in the treatment of the aforementioned disorders and diseases in an afflicted mammal.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the Formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

The compounds of formula I and their pharmaceutically acceptable salts exhibit substance P receptor-binding activity and therefore are of value in the treatment and prevention of a wide variety of clinical conditions the treatment or prevention of which are effected or facilitated by a decrease in substance P mediated neurotransmission. Such conditions include urinary incontinence, inflammatory diseases (e.g., arthritis, psoriasis, asthma and inflammatory bowel disease), reflux gastroesophogal disease, hypertension, anxiety, depression or dysthymic disorders, colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis. Hence, these compounds are readily adapted to therapeutic use as substance P antagonists for the control and/or treatment of any of the aforesaid clinical conditions in mammals, including humans.

The compounds of the formula I and the pharmaceutically acceptable salts thereof can be administered via either the oral, parenteral or topical routes. In general, these compounds are most desirably administered in dosages ranging from about 5.0 mg up to about 1500 mg per day, although variations will necessarily occur depending upon the weight and condition of the subject being treated and the particular route of administration chosen. However, a dosage level that is in the range of about 0.07 mg to about 21 mg per kg of body weight per day is most desirably employed. Variations may nevertheless occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

The compounds of the invention may be administered alone or in combination with pharmaceutically acceptable carriers or diluents by any one of the three routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a therapeutic compound of the present invention in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The activity of the compounds of the present invention as substance P antagonists may be determined by their ability to inhibit the binding of substance P at its receptor sites in bovine caudate tissue, employing radioactive ligands to visualize the tachykinin receptors by means of autoradiography. The substance P antagonizing activity of the herein described compounds may be evaluated by using the standard assay procedure described by M. A. Cascieri et al., as reported in the *Journal of Biological Chemistry*, Vol. 258, p. 5158 (1983). This method essentially involves determining the concentration of the individual compound required to reduce by 50% the amount of radiolabelled substance P ligands at their receptor sites in said isolated cow tissues, thereby affording characteristic $IC_{50}$ values for each compound tested.

In this procedure, bovine caudate tissue is removed from a −70° C. freezer and homogenized in 50 volumes (w./v.) of an ice-cold 50 mM Tris (i.e., trimethamine which is 2-amino-2-hydroxymethyl-1,3-propanediol) hydrochloride buffer having a pH of 7.7. The homogenate is centrifuged at 30,000×G for a period of 20 minutes. The pellet is resuspended in 50 volumes of Tris buffer, rehomogenized and then recentrifuged at 30,000×G for another twenty-minute period. The pellet is then resuspended in 40 volumes of ice-cold 50 mM Tris buffer (pH 7.7) containing 2 mM of calcium chloride, 2 mM of magnesium chloride, 40 g/ml of bacitracin, 4 µg/ml of leupeptin, 2 µg of chymostatin and 200 g/ml of bovine serum albumin. This step completes the production of the tissue preparation.

The radioligand binding procedure is then carried out in the following manner, viz., by initiating the reaction via the addition of 100 µl of the test compound made up to a concentration of 1 µM, followed by the addition of 100 µl of radioactive ligand made up to a final concentration 0.5 mM and then finally by the addition of 800 µl of the tissue preparation produced as described above. The final volume is thus 1.0 ml, and the reaction mixture is next vortexed and incubated at room temperature (ca. 20° C.) for a period of 20 minutes. The tubes are then filtered using a cell harvester, and the glass fiber filters (Whatman GF/B) are washed four times with 50 mM of Tris buffer (pH 7.7), with the filters having previously been presoaked for a period of two hours prior to the filtering procedure. Radioactivity is then determined in a Beta counter at 53% counting efficiency, and the $IC_{50}$ values are calculated by using standard statistical methods.

The anti-psychotic activity of the compounds of the present invention as neuroleptic agents for the control of various psychotic disorders may be determined by a study of their ability to suppress substance P-induced or substance P agonist induced hypermotility in guinea pigs. This study is carried out by first dosing the guinea pigs with a control compound or with an appropriate test compound of the present invention, then injecting the guinea pigs with substance P or a substance P agonist by intracerebral administration via canula and thereafter measuring their individual locomotor response to said stimulus.

The present invention is illustrated by the following examples. It will be understood, however, that the invention is not limited to the specific details of these examples.

EXAMPLE 1

(2S,3S)-3-(2-Methoxybenzyl)amino-2-phenyl-1-[4-(thiazol-2-yl)aminobutyl]piperidine Hydrochloride In a round-bottom flask were placed 100 mg (0.27 mmol) of (2S,3S)-1-(4-aminobutyl)-3-(2-methoxybenzyl)amino-2-phenylpiperidine and 0.5 mL of water. To the system were added 57 mg (0.54 mmol) of sodium carbonate and 25 µL of 2-bromothiazole, and the mixture was heated at 60° C. overnight. The mixture was heated at 80°–90° C. for an additional day. During this period, 0.5 mL of isopropanol and 0.5 mL of 2-bromothiazole were added to the system. The mixture was partitioned between chloroform and saturated aqueous sodium bicarbonate and extracted with two portions of chloroform. The combined chloroform extracts were dried ($Na_2SO_4$) and concentrated. The crude brown oil was purified by flash column chromatography (35 g of silica gel) using 1:3 methanol/chloroform as the eluant to obtain 38 mg of product. This material was dissolved in ethyl acetate, and ether saturated with hydrogen chloride (HCl) was added to the solution. The solvent was removed with a pipet and the residue was subjected to high vacuum to obtain 21 mg of the title compound, mp 90°–95° C.

$^1$H NMR ($CDCl_3$) δ 1.20 (m, 1H), 1.50 (m, 3H), 1.76 (m, 3H), 2.02 (m, 3H), 2.56 (m, 2H), 3.20 (m, 3H), 3.28 (d, 1H, J=2), 3.38 (d, 1H, J=15), 3.46 (s, 3H), 3.66 (d, 1H, J=15), 5.80 (br s, 1H), 6.39 (d, 1H, J=3), 6.60 (d, 1H, J=9), 6.70 (t, 1H, J=6), 6.81 (d, 1H, J=6), 7.04 (m, 2H), 7.26 (m, 5H). HRMS calc'd for $C_{26}H_{34}N_4OS$: 450.2457. Found: 450.2411.

EXAMPLE 2

(2S,3S)-3-(2-Methoxybenzyl)amino-2-phenyl-1-[4-(pyrimidin-2-yl)aminobutyl]piperidine Hydrochloride The title compound was prepared in a similar manner to the compound of Example 1 by replacing 2-bromothiazole with 2-chloropyrimidine; mp 123°–127° C. (dec.) $^1$H NMR ($CDCl_3$) 67 1.46 (m, 5H), 1.94 (m, 6H), 2.54 (m, 2H), 3.24 (m, 4H), 3.35 (d, 1H, J=15), 3.48 (s, 3H), 3.64 (d, 1H, J=15), 6.42 (t, 1H, J=5), 6.59 (d, 1H, J=9), 6.68 (t, 1H, J=6), 6.80 (d, 1H, J=6), 7.05 (t, 1H, J=9), 7.22 (m, 5H), 8.18 (d, 2H, J=5). HRMS calc'd for $C_{27}H_{35}N_5O$: 445.2836. Found: 445.2813.

EXAMPLE 3 cis-1-[4-(Benzoxazol-2-yl)aminobutyl]-3-(2-methoxybenzyl)amino-2-phenylpiperidine Hydrochloride The title compound was prepared in a similar manner to the compound of Example 1 by replacing (2S, 3S)-3-(2-methoxybenzyl)amino-2-phenylpiperidine with the corresponding racemate and 2-bromothiazole with 2-chlorobenzoxazole; mp 158°–160° C. (dec.) $^1$H NMR ($CDCl_3$) 67 1.58 (m, 5H), 1.90 (m, 1H), 2.04 (m, 4H), 2.20 (m, 1H), 2.56 (m, 1H), 2.71 (d, 1H, J=2), 3.25 (m, 1H), 3.38 (m, 5H), 3.57 (d, 1H, J=15), 3.96 (d, 1H, J=15), 6.60 (d, 1H, J=6), 6.76 (t, 1H, J=6), 6.96 (m, 2H), 7.12 (m, 3H), 7.28 (m, 6H). HRMS calc'd for $C_{30}H_{36}N_4O_2$: 484.2838. Found: 484.2844.

EXAMPLE 4 cis-3-(2-Methoxybenzyl)amino-1-[4-oxo-4-(thien-2-yl)butyl]-2-phenylpiperidine

Under a nitrogen atmosphere, in a round-bottom flask were placed 200 mg (0.68 mmol) of cis-3-(2-methoxybenzyl)amino-2-phenylpiperidine and 0.6 mL of tetrahydrofuran. To the system were added 95 µL of triethylamine and 0.11 mL (0.68 mmol) of 4-chloro-1-oxo-1-(thien-2-yl)butane, and the mixture was heated at 75° C. for 1 day. The reaction mixture was partitioned between chloroform and saturated aqueous sodium bicarbonate and extracted with three portions of chloroform. The combined extracts were dried using sodium sulfate ($Na_2SO_4$) and concentrated. The crude product was purified by flash column chromotography (20 g of silica gel) using 1:19 methanol/chloroform as the eluant to obtain pure title compound as its free base. This material was dissolved in ethyl acetate, and the ether saturated with HCl was added to the solution. Filtration of the resulting suspension afforded the title compound as a hygroscopic solid, mp 69°–74° C. $^1$H NMR ($CDCl_3$) 67 1.22 (m, 1H), 1.50 (m, 2H), 2.00 (m, 5H), 2.66 (m, 3H), 2.88 (m, 1H), 3.24 (m, 1H), 3.35 (d, 1H, J=2), 3.40 (d, 1H, J=15), 3.48 (s, 3H), 3.70 (d, 1H, J=15), 6.65 (d, 1H, J=6), 6.76 (t, 1H, J=6), 6.88 (d, 1H, J=6), 7.10 (m, 2H), 7.28 (m, 4H), 7.58 (m, 1H), 7.66 (d, 1H, J=2). Mass spectrum: m/z 448 (parent).

EXAMPLE 5

(2S,3S)-1-[2,3-(Dihydro-3-oxobenzisosulfonazol-2-yl)butyl]-3-(2-methoxybenzyl)amino-2-phenylpiperidine Hydrochloride The title compound was prepared in a similar manner to the compound of Example 4 by replacing cis-3-(2- methoxybenzylamino)-2-phenylpiperidine with the corresponding (2S, 3S)-enantiomer and the substituted chlorobutane with 1-bromo-4-(2,3-dihydro-3-oxobenzisosulfonazol-2-yl)butane: mp 120°–122° C. $^1$H NMR (CDCl$_3$) δ 1.60 (m, 6H), 2.02 (m, 4H), 2.58 (m, 2H), 3.22 (m, 1H), 3.31 (d, 1H, J=3), 3.37 (d, 1H, J=15), 3.47 (s, 3H), 3.68 (m, 3H), 6.62 (d, 1H, J=6), 6.73 (t, 1H, J=9), 6.86 (d, 1H, J=9), 7.09 (t, 1H, J=6), 7.26 (m, 5H), 7.82 (m, 3H), 8.00 (m, 1H). HRMS calc'd for C$_{30}$H$_{25}$N$_3$O$_4$S: 533.2344. Found: 533.2354.

EXAMPLE 6 cis-3-(2-Methoxybenzyl)amino-2-phenyl-1-[4-succinimido-1-yl)butyl]piperidine Hydrochloride The title compound was prepared in a similar manner to the compound of Example 4 by replacing the substituted chlorobutane with 4-(succinimido-1-yl)-1-methylsulfonyloxybutane [prepared from 4-amino-1-butanol by sequential treatment with succinic anhydride (xylenes, acetic anhydride, reflux, 2 hours), sodium methoxide (methanol, 3 hours) and methanesulfonyl chloride (triethylamine, THF, 3h)]. $^1$H NMR (CDCl$_3$) δ 1.40 (m, 4H), 1.60 (m, 1H), 1.94 (m, 1H), 1.96 (m, 2H), 2.34 (m, 1H), 2.46 (m, 1H), 2.60 (m, 4H), 3.14 (m, 1H), 3.20 (d, 1H, J=2), 3.34 (m, 6H), 3.51 (m, 1H), 3.62 (m, 2H), 6.56 (d, 1H, J=9), 6.67 (t, 1H, J=9), 6.78 (d, 1H, J=6), 7.03 (t, 1H, J=6), 7.18 (m, 5H). HRMS calc'd for C$_{27}$H$_{35}$N$_3$O$_3$: 449.2678. Found: 449.2678.

EXAMPLE 7

(2S,3S)-1-(5,6-Carbonyldioxyhexyl)-3-(2-methoxybenzyl)amino-2-phenylpiperidine Hydrochloride Under a nitrogen atmosphere, in a round-bottom flask were placed 0.15 mmol of (2S,3S)-1-(5,6-dihydroxyhexyl)-3-(2-methoxybenzyl)amino-2-phenylpiperidine and 0.5 ml of CHCl$_3$. To the system was added 49 mg (0.30 mmol) carbonyldiimidazole. The mixture was heated at 60°–75° C. for 5 days. During this period, additional (325 mg) carbonyldiimidazole, CHCl$_3$ (0.5 ml), and THF (0.5 ml) were added to the system. The reaction mixture was partitioned between chloroform and saturated aqueous sodium bicarbonate and extracted with two portions of chloroform. The combined extracts were washed with water, dried (Na$_2$SO$_4$) and concentrated. The crude product was purified by flash column chromatography (1.5 g of silica gel) using 1:9 methanol/chloroform as the eluant to obtain 35 mg of product. This material was dissolved in ethyl acetate, and ether saturated with HCl was added to the solution. Solvent was removed from the resulting suspension using a pipet, and the residue was subjected to high vacuum to afford 17 mg of the title compound, mp 73°–76° C. (dec). $^1$H NMR (CDCl$_3$) δ 1.26 (m, 2H), 1.50 (m, 4H), 1.70 (m, 2H), 1.94 (m, 1H), 2.04 (m, 3H), 2.58 (m, 2H), 3.22 (m, 1H), 3.30 (d, 1H, J=2), 3.38 (d, 1H, J=15), 3.47 (s, 3H), 3.70 (d, 1H, J=15), 4.00 (m, 1H), 4.44 (m, 1H), 4.60 (m, 1H), 6.64 (d, 1H, J=9), 6.75 (t, 1H, J=6), 6.85 (d, 1H, J=6), 7.10 (t, 1H, J=9), 7.26 (m, 5H). HRMS calc'd for C$_{23}$H$_{34}$N$_2$O$_4$: 438.2518. Found: 438.2521.

EXAMPLE 8 cis-3-(2-Methoxybenzyl)amino-2-phenyl)-1-[4-(thien-2-yl)butyl]piperidine

The title compound was prepared in a similar manner to the compound of Example 4 by replacing the chlorobutane with 1-methylsulfonyloxy-4-(thien-2-yl) butane. $^1$H NMR (CDCl$_3$) δ 1.32–1.6 (m, 6H), 1.96–2.3 (m, 4H), 2.50–2.72 (m, 4H), 2.8–2.9 (m, 1H), 3.16–3.38 (m, 3H), 3.40 (s, 3H), 3.65–3.80 (m, 1H), 6.59–6.76 (m, 3H), 6.81–6.88 (m, 2H), 7.02–7.12 (m, 2H), 7.20–7.38 (m, 5H). Mass spectrum: m/z 434 (parent).

I claim:
1. A compound having the formula

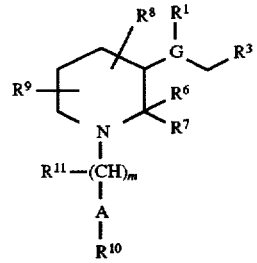

wherein m is an integer from 1 to 8, and any one of the carbon—carbon single bonds of (CH$_2$)$_m$ may optionally be replaced by a carbon—carbon double bond or a carbon—carbon triple bond, and any one of the carbon atoms of said (CH$_2$)$_m$ may optionally be substituted with R$^{11}$;

R$^1$ is hydrogen or (C$_1$–C$_8$) alkyl optionally substituted with hydroxy, alkoxy or fluoro;

R$^3$ is aryl selected from phenyl, indanyl and naphthyl; heteroaryl selected from benzothienyl, benzofuryl, thienyl, furyl, pyridyl, thiazolyl, isothiazolyl, oxazolyl, isoxazolyl, triazolyl, tetrazolyl, and quinolyl; or cycloalkyl having from three to seven carbon atoms, wherein one of said carbon atoms may optionally be replaced by nitrogen, oxygen or sulfur; wherein each of said aryl and heteroaryl groups may optionally be substituted with one or more substituents, and said (C$_3$–C$_7$)cycloalkyl may optionally be substituted with one or two substituents, said substituents being independently selected from halo, nitro, (C$_1$–C$_{10}$)alkyl optionally substituted with from one to three fluorine atoms, (C$_1$–C$_{10}$)alkoxy optionally substituted with from one to three fluorine atoms, trifluoromethyl, amino, (C$_1$–C$_6$)-alkylamino, di(C$_1$–C$_6$) alkylamino,

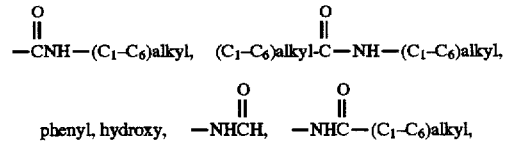

hydroxy(C$_1$–C$_6$)alkyl, and (C$_1$–C$_6$)alkoxy(C$_1$–C$_6$)alkyl;

R$^6$ is a functionality selected from hydrogen, (C$_1$–C$_6$) straight or branched alkyl, (C$_3$–C$_7$)cycloalkyl wherein one of the carbon atoms may optionally be replaced by nitrogen, oxygen or sulfur; aryl selected from biphenyl, phenyl, indanyl and naphthyl; heteroaryl selected from benzothienyl, thienyl, furyl, benzofuryl, pyridyl, thiazolyl, isothiazolyl, oxazolyl, isoxazolyl, triazolyl, tetrazolyl and quinolyl; phenyl(C$_2$–C$_6$)alkyl, benzhydryl and benzyl, wherein each of said aryl and heteroaryl groups and the phenyl moieties of said benzyl, phenyl(C$_2$–C$_6$)alkyl and benzhydryl may optionally be substituted with one or more substituents independently selected from halo, nitro, (C$_1$–C$_{10}$)alkyl optionally substituted with from one to three fluorine atoms, (C$_1$–C$_{10}$)alkoxy optionally substituted with from one to three fluorine atoms, amino, hydroxy(C$_1$–C$_6$)alkyl, $(C_1-C_6)$alkoxy$(C_1-C_6)$alkyl, $(C_1-C_6)$-alkylamino,

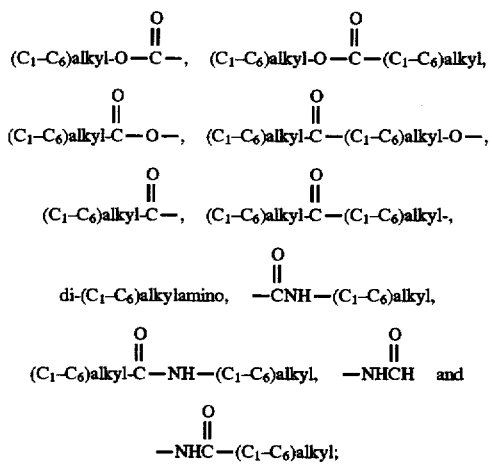

and wherein one of the phenyl moieties of said benzhydryl may optionally be replaced by naphthyl, thienyl, furyl or pyridyl;

$R^7$ is hydrogen, phenyl or $(C_1-C_6)$alkyl;

or $R^6$ and $R^7$, together with the carbon to which they are attached, form a saturated carbocyclic ring having from 3 to 7 carbon atoms wherein one of said carbon atoms may optionally be replaced by oxygen, nitrogen or sulfur;

$R^8$ may be attached to any atom of the nitrogen containing ring having an available bonding site and $R^9$ may be attached to any carbon atom of the nitrogen containing ring having an available bonding site;

$R^8$ and $R^9$ are independently selected from hydrogen, hydroxy, halo, amino, oxo (=O), cyano, hydroxy-$(C_1-C_6)$alkyl, $(C_1-C_6)$alkoxy-$(C_1-C_6)$alkyl, $(C_1-C_6)$ alkylamino, di-$(C_1-C_6)$alkylamino, $(C_1-C_6)$alkoxy,

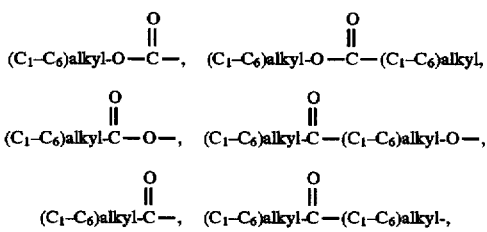

and the functionalities set forth in the definition of $R^6$;

A is selected from the group consisting of $CH_2$, nitrogen, oxygen, sulfur and carbonyl;

G is nitrogen, oxygen or sulfur;

$R^{10}$ is a monocyclic or bicyclic heterocycle selected from the group consisting of pyrimidinyl, benzoxazolyl, 2,3-dihydro-3-oxobenzisosulfonazol-2-yl, succinimidyl or thienyl;

$R^{11}$ is oximino (=NOH) or one of the functionalities set forth in any of the definitions of $R^6$, $R^8$ and $R^9$; and with the proviso that a) neither $R^8$, $R^9$, $R^{10}$ nor $R^{11}$ can form, together with the carbon to which it is attached, a ring with $R^7$, (b) when $R^8$ and $R^9$ are attached to the same carbon atom, then either each of $R^8$ and $R^9$ is independently selected from hydrogen, fluoro, $(C_1-C_6)$ alkyl, hydroxy-$(C_1-C_6)$alkyl, and $(C_1-C_6)$alkoxy-$(C_1-C_6)$alkyl; or $R^8$ and $R^9$, together with the carbon to which they are attached, form a $(C_3-C_6)$saturated carbocyclic ring that forms a spiro compound with the nitrogen containing ring to which they are attached, (c) when A is nitrogen, sulfur or oxygen, m is greater than one, (d) when A is $CH_2$ or carbonyl then $R^{10}$ must be substituted or unsubstituted pyrimidinyl, benzoxazolyl, 2,3-dihydro-3-oxobenzisosulfonazol-2-yl, or succinimidyl; (e) when G is oxygen or sulfur then $R^1$ is absent.

2. A compound according to claim 1, wherein G is nitrogen.

3. A compound according to claim 1 wherein m is an integer from 4 to 6; G is nitrogen; $R^3$ is phenyl, optionally substituted with one or two substituents, said substituents being independently selected from halo, nitro, $(C_1-C_{10})$ alkyl optionally substituted with from one to three fluorine atoms, $(C_1-C_{10})$ alkoxy optionally substituted with from one to three fluorine atoms, trifluoromethyl, amino, $(C_1-C_6)$-alkylamino, di$(C_1-C_6)$alkylamino,

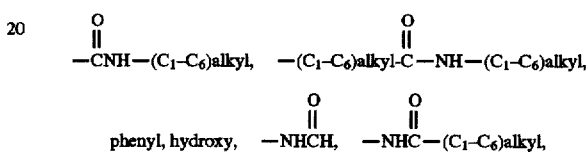

hydroxy$(C_1-C_6)$alkyl, and $(C_1-C_6)$alkoxy$(C_1-C_6)$alkyl; $R^6$ is phenyl; $R^7$ is hydrogen; and $R^1$ is hydrogen.

4. A compound according to claim 3 wherein $R^1$, $R^8$, $R^9$ and $R^{11}$ are hydrogen.

5. A compound according to claim 1 wherein said compound is selected from (2S,3S)-3 -(2-methoxybenzyl) amino-2-phenyl-1-[4-(thiazol-2-yl)aminobutyl]piperidine;

(2S,3S)-3-(2-methoxybenzyl)amino-2-phenyl-1-[4-(pyrimidin-2-yl)aminobutyl]piperidine;

cis-1-[4-(benzoxazol-2-yl)aminobutyl]-3-(2-methoxybenzyl)amino-2-phenylpiperidine;

(2S,3S)-1-[2,3-(dihydro-3-oxobenzisosulfonazol-2-yl) butyl]-3-(2-methoxybenzyl)amino-2-phenylpiperidine;

cis-3-(2-methoxybenzyl)amino-2-phenyl-1-[4-(succinimido-1-yl)butyl]piperidine; and (2S,3S)-1-(5,6-carbonyldioxyhexyl)-3-(2-methoxybenzyl)amino-2-phenylpiperidine.

6. A pharmaceutical composition for treating or preventing a condition selected from the group consisting of inflammatory diseases, reflux gastroesophogal disease, hypertension anxiety, depression or dysthymic disorders, cluster headache, colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders, diabetic neuropathy and multiple sclerosis, disorders related to immune enhancement or suppression such as systemic lupus erythematosus, and rheumatic diseases such as fibrositis in a mammal, including a human, comprising an amount of a compound according to claim 1 effective in preventing or treating such condition and a pharmaceutically acceptable carrier.

7. A method of treating or preventing a condition selected from the group consisting of inflammatory diseases, reflux gastroesophogal disease, hypertension, anxiety, depression or dysthymic disorders, cluster headache, colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders, diabetic neuropathy and multiple sclerosis, disorders related to immune enhancement or suppression such as systemic lupus erythematosus, and rheumatic diseases such as fibrositis in a mammal, including a human, comprising administering to a mammal in need of such treatment or prevention an amount of a compound according to claim 1 effective in preventing or treating such condition.

* * * * *